United States Patent [19]

Marlin

[11] Patent Number: 5,715,451
[45] Date of Patent: Feb. 3, 1998

[54] METHOD AND SYSTEM FOR CONSTRUCTING FORMULAE FOR PROCESSING MEDICAL DATA

[75] Inventor: Tom Marlin, Edmonds, Wash.

[73] Assignee: SpaceLabs Medical, Inc., Redmond, Wash.

[21] Appl. No.: 504,703

[22] Filed: Jul. 20, 1995

[51] Int. Cl.$^6$ .................................................. G06F 17/30
[52] U.S. Cl. ........................... 395/615; 395/202; 395/203
[58] Field of Search .................... 395/615, 202, 395/203; 364/413.02, 413.09, 413.01, 413.06; 128/642, 670, 671

[56] References Cited

U.S. PATENT DOCUMENTS

| | | | |
|---|---|---|---|
| 4,878,175 | 10/1989 | Borden-Paul et al. | 395/203 |
| 5,018,067 | 5/1991 | Mohlenbrock et al. | 364/413.02 |
| 5,072,383 | 12/1991 | Brimm et al. | 364/413.02 |
| 5,077,666 | 12/1991 | Brimm et al. | 364/202 |
| 5,199,439 | 4/1993 | Zimmerman et al. | 128/670 |
| 5,235,510 | 8/1993 | Yamada et al. | 364/413.02 |
| 5,262,943 | 11/1993 | Thibado et al. | 364/413.01 |
| 5,265,010 | 11/1993 | Evans-Pageneli et al. | 364/413.02 |
| 5,299,119 | 3/1994 | Kraf et al. | 364/413.06 |
| 5,307,262 | 4/1994 | Ertel | 364/413.01 |
| 5,307,263 | 4/1994 | Brown | 364/413.09 |
| 5,348,008 | 9/1994 | Bornn et al. | 128/642 |
| 5,375,604 | 12/1994 | Kelly et al. | 128/671 |
| 5,404,292 | 4/1995 | Hendrickson | 364/413.02 |
| 5,546,580 | 8/1996 | Seliger et al. | 395/615 |

OTHER PUBLICATIONS

Kahn et al, Extensions to the time–Oriented Database Model Support Temporal Reasoning in Medical Expert Systems, Internet, abstract, Apr. 1991.

Kahn et al, Model–Based Interpretation of Time–Varying Medical Data, Internet, abstract, Dec. 1989.

Collet et al, Real–Time Trend Analysis for an Intensive Care Unit Patient Data Management System, IEEE, pp.337–344, Jun. 1990.

"System Administrator Guide," SpaceLabs Medical, Inc. PC Chartmaster, pp. Calcs–1–Calcs–6, 1994.

*Primary Examiner*—Wayne Amsbury
*Assistant Examiner*—Frantz Coby
*Attorney, Agent, or Firm*—Seed and Berry LLP

[57] ABSTRACT

A method and system for constructing formulae for processing medical data is provided by a formula construction facility. In a preferred embodiment, the facility displays a list of time-indexed medical values. A user selects the name of a time-indexed medical value from the displayed list. The facility also displays a list of time intervals for qualifying individual values of the identified time-indexed medical value. The user similarly selects an interval from the displayed list of time intervals. The facility further displays a list of functions for reducing the individual values of the selected time-indexed medical value whose effective times are within the identified time interval to a single value. In response, the user selects a function from the displayed list of functions. The facility then stores a formula for applying the selected function to individual values of the selected time-indexed medical value whose effective times are within the selected time interval in order to reduce the individual values to a single value.

14 Claims, 10 Drawing Sheets

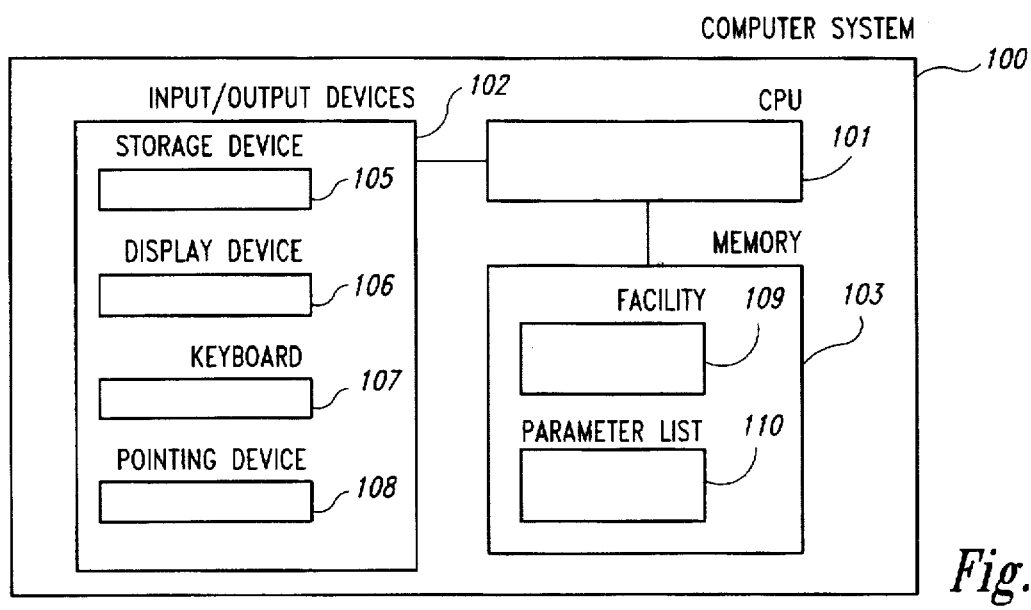
*Fig. 1*
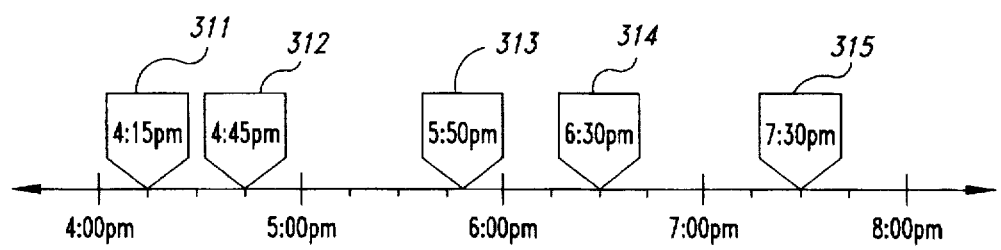
*Fig. 2*
*Fig. 3*

METHOD AND SYSTEM FOR CONSTRUCTING FORMULAE FOR PROCESSING MEDICAL DATA

CROSS-REFERENCE TO RELATED APPLICATION

U.S. patent application Ser. No. 08/504,801, filed Jul. 20, 1995, now pending, and entitled "METHOD AND SYSTEM FOR FLEXIBLY ORGANIZING, RECORDING, AND DISPLAYING MEDICAL PATIENT CARE INFORMATION," contains subject matter related to the present application.

TECHNICAL FIELD

The invention relates generally to the field of medical data processing, and, more specifically, to the field of constructing formulae for processing medical data.

BACKGROUND OF THE INVENTION

The provision of health care services to patients depends on the maintenance of significant quantities of clinical patient information. Health care providers have traditionally maintained such patient information manually on physical charts comprised of paper forms.

There are many incentives to automate patient information maintenance. Doing so facilitates viewing and modifying information for a particular patient in number of different locations simultaneously, automatically collecting data from medical sensors and medical laboratories, and making the patient information relatively immutable.

Traditional methods of making patient care decisions require health care professionals to review and draw inferential conclusions from relatively large quantities of raw, observable patient information. However, if patient information is collected and maintained in electronic form, it becomes desirable to provide means for manipulating the raw patient information to produce higher-level patient information that provides a more useful basis for health care decisions. Such manipulations would optimally be customizable by individual health care organizations to meet their unique needs for supporting patient care decisions.

SUMMARY OF THE INVENTION

The present invention provides a method and system for constructing formulae for processing medical data. In a preferred embodiment, users interact with a formula generation facility ("the facility") in order to construct a formula for a time-indexed medical output parameter that is based on time-indexed medical input parameters. The facility presents the user with an intuitive and comprehensive visual interface for constructing a formula for processing such input parameters. The facility permits users to easily select an output parameter for which the formula will generate values and select the input parameters from which the formula will generate values, apply summary functions as well as mathematical and logical operators and comparators, and specify time intervals of the input parameters relative to the output parameters. Formulae constructed using the facility may be used to generate higher-level patient information, and even to generate preliminary medical judgments and treatment recommendations. To the extent that a formula is generalizable among different patients, a formula constructed for one patient may be used to generate its output parameter for other patients.

BRIEF DESCRIPTION OF THE DRAWINGS

FIG. 1 is a high-level block diagram of the general-purpose computer system upon which the facility preferably operates.

FIG. 2 is a diagram showing events stored for a Heart Rate parameter.

FIG. 3 is a timing diagram showing the relative event times of the events shown in FIG. 2.

DERAILED DESCRIPTION OF THE INVENTION

Figure 4:
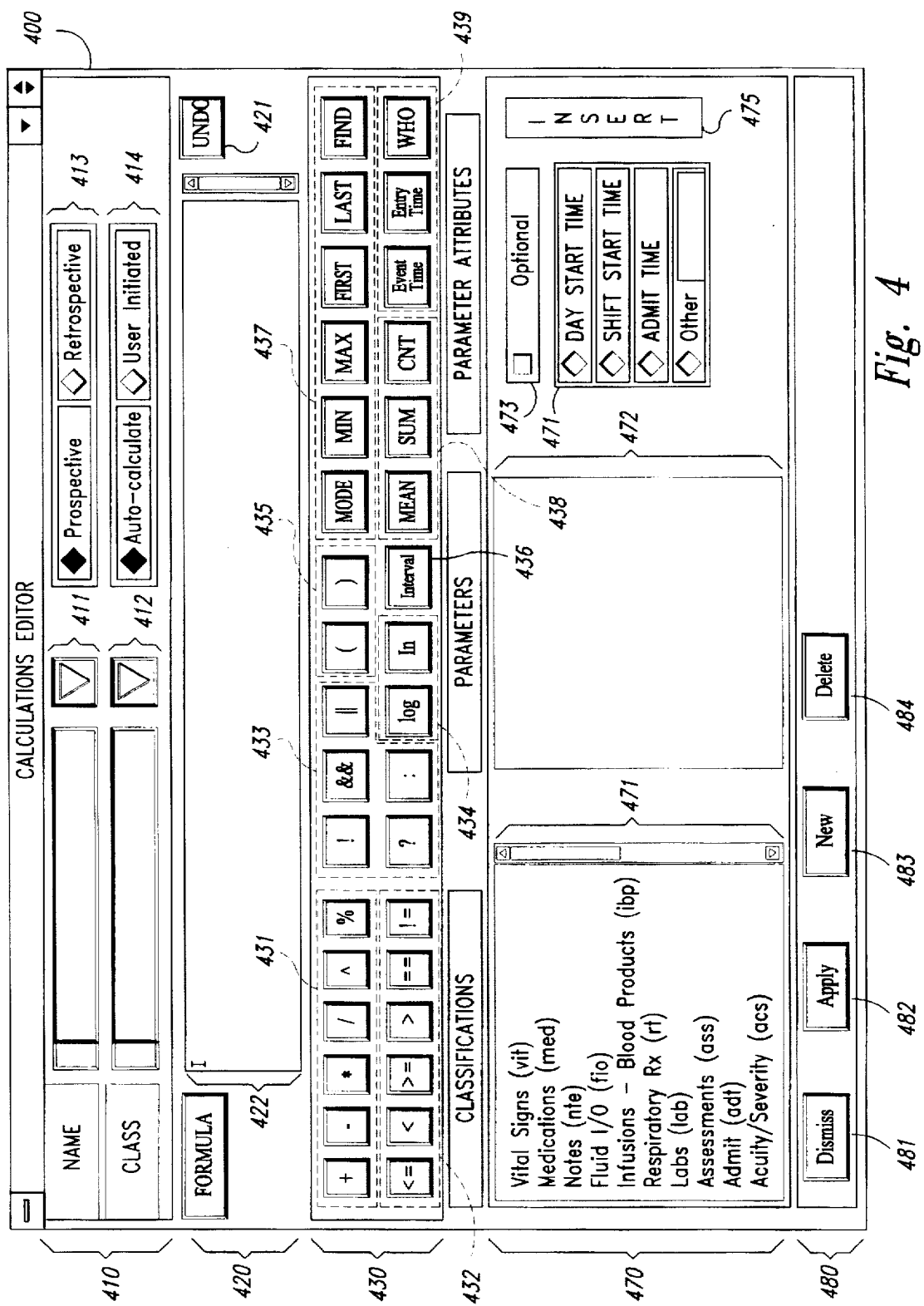
FIG. 4 is a screen diagram showing details of the visual interface presented by the facility.

The present invention provides a method and system for constructing formulae for processing medical dam. In a preferred embodiment, users interact with a formula construction facility ("the facility") in order to construct a formula for a time-indexed medical output parameter that is based on time-indexed medical input parameters. The facility presents the user with an intuitive and comprehensive visual interface for constructing a formula for processing such input parameters. The facility permits users to easily select an output parameter for which the formula will generate values and select the input parameters from which the formula will generate values, apply summary functions as well as mathematical and logical operators and comparators, and specify time intervals of the input parameters relative to the output parameters. Details of the appearance of the visual interface presented by the facility are shown in FIG. 4, discussed in detail below. Formulae constructed using the facility may be used to generate higher-level patient information, and even to generate preliminary medical judgments and treatment recommendations. To the extent that a formula is generalizable among different patients, a formula constructed for one patient may be used to generate its output parameter for other patients.

The facility is particularly useful when employed in conjunction with an automated medical information system for flexibly structuring, receiving, and presenting medical patient information. An example of such an automated medical patient information system is discussed in detail in U.S. application Ser. No. 08/504,801, which is filed concurrently herewith and is hereby incorporated by reference, now pending.

FIG. 1 is a high-level block diagram of the general-purpose computer system upon which the facility preferably operates. The computer system 100 contains a central processing unit (CPU) 101, input/output devices 102, and a computer memory (memory) 103. Among the input/output devices 102 is a storage device 105, such as a hard disk drive; a display device 106, such as a video monitor; a keyboard 107; and a pointing device 108, such as a mouse. The computer programs that preferably comprise the facility 109 reside in the memory 103 and execute on the CPU 101. The memory 103 preferably also contains a list of patient parameters 110. While the facility is preferably implemented on a computer system configured as described above, one skilled in the art will recognize that it may also be implemented on computer systems having different configurations.

The medical data processed by the constructed formulae is preferably organized into parameters, which correspond to different characteristics of a patient's condition that may be measured or otherwise determined and used by health care personnel to evaluate and treat the patient. For example, different parameters may correspond to temperature, heart rate, and cough assessment. For a patient, each parameter may have several events stored for it. Each stored event describes the measure or state at a particular time of the characteristic of patient condition to which the parameter corresponds. For instance, if the patient's heart rate is measured as 35 beats per minute at 10:40 a.m. and as 42 beats per minute at 11:15 a.m., two events will be stored for the Heart Rate parameter: a first event having a value of 35 and a time of 10:40 a.m., and a second event having a value of 42 and a time of 11:15 a.m. Because each event value stored for the utilized parameters is stored in conjunction with its event time, the parameters are said to be "time-indexed." In addition to value and event time, other data may also be stored for each event. For instance, the identity of the person or device that entered the event and the time at which the event was entered may also be stored for each parameter.

FIG. 2 is a diagram showing events stored for the Heart Rate parameter. For the period between 4:00 p.m. and 8:00 p.m., events 211–215 are shown. Each event comprises an event time 201 at which the event occurred; an event value 202, which in this case represents heart rate in beats per minute; an entry time 203 at which the event was entered or stored; and the name of the person who entered the event 204. FIG. 3 is a timing diagram showing the relative event times of the events shown in FIG. 2. FIG. 3 shows event 311 at 4:15 p.m., event 312 at 4:45 p.m., event 313 at 5:50 p.m., event 314 at 6:30 p.m., and event 315 at 7:30 p.m.

Users interact with the facility in order to construct a formula for a time-indexed output parameter that is based on time-indexed input parameters. Once constructed, the formula may be used to generate events for the output parameter. Each generated output parameter event is based on events that have been stored for the formula's input parameters that have event times within a time interval defined relative to the event time of the output parameter event. The time interval for each input parameter may be specified, relative to the time of the output parameter of event, within the formula constructed using the facility. If no interval is specified for an input parameter of a formula, the facility preferably uses one of the time intervals defined by the automated medical information system to display events of the input and output parameters. The automated medical information system preferably permits users to adjust this display interval. The facility therefore preferably determines and uses the current display interval at the time it applies the constructed formula to generate output parameter events.

As an example, it may be useful to maintain a "highest recent heart rate" parameter corresponding to highest heart rate value stored for a patient in the last two hours. In such a case, a user would use the facility to construct a formula for generating events for the Highest Recent Heart Rate parameter using the Heart Rate parameter. For a particular event of the Highest Recent Heart Rate parameter, the constructed formula would specify identifying the events of the Heart Rate parameter having event times between the event time of the event of the Highest Recent Heart Rate parameter and two hours before the event time of the event of the Highest Recent Heart Rate parameter. For example, if such a formula was applied to the heart rate events shown in FIG. 3, for an output parameter event time of 6:00 p.m., the formula would identify events 311,312, and 313. The formula would further specify subjecting the identified events to a Maximum event selection function, which returns the event among those identified as within the interval having the largest value.

FIG. 4 is a screen diagram showing details of the visual interface presented by the facility. The visual interface 400 is divided into an output parameter area 410, a formula area 420, a manipulator area 430, an input parameter area 470, and a command area 480.

The output parameter area 410 is for specifying the output parameter that is to contain the constructed formula and its attributes. The output parameter area 410 contains output parameter selection controls 411–412 and output parameter attribute selection controls 413–414. The parameters are preferably divided into classifications that group the parameters in a meaningful way. The user uses output parameter selection control 412 to select the classification of the output parameter. The user uses output parameter selection control 411 to select the name of the output parameter from a list of the parameters contained by the selected classification. Output parameter attribute selection control 413 allows the user to specify how the time interval specified for each input parameter relates to the event time for the output parameter. Output parameter attribute selection control 414 allows the user to select whether the formula will be used to calculate values of the output parameter automatically, or only in response to a specific user instruction.

The formula area 420 is for displaying the formula during its construction. The formula area 420 contains a formula window 422 in which the formula is constructed and displayed. The formula window also contains an insertion point 423 that indicates the point within the formula at which additional formula contents will be inserted. The user may move the insertion point to any point within the formula window 422 using either the pointing device 108 or cursor movement keys of the keyboard 107. The user may insert additional formula contents into the formula at the insertion point 423 by typing them using the keyboard 107, or by using the buttons in the manipulator area 430 and the input parameter area 470 as discussed below. The formula area 420 also contains an undo button 421, which the user may press to remove the last insertion from the formula.

The manipulator area 430 contains buttons that the user may use to insert value manipulators, such as operators and functions, into the formula at the insertion point. Among the buttons in the manipulation area 430 are: arithmetic operator buttons 431 for inserting operators for the addition, subtraction, multiplication, division, exponentation, and modulo operations; comparison operator buttons 432, for inserting less than or equal to, less than, greater than or equal to, greater than, equal to, and not equal to comparison operators; logical operator insertion buttons 433, including buttons for inserting not, and, or, and value-branching logical operators; mathematical function buttons 434 for inserting the log and natural log functions; grouping buttons 435, for inserting parentheses in order to group quantities; interval button 436, for inserting the length of a special interval for reporting parameter event values; selection function buttons 437 for inserting the mode, minimum, maximum, first, last, and find event selection functions described below; aggregation function buttons 438 for inserting the mean, sum, and count aggregation functions described below; and the event modifier buttons 439 for inserting the event time, entry time, and who event modifiers as described below. The addition button in the arithmetic operator buttons 431 may also be used to insert a string concatenation operator for joining the contents of two strings.

The input parameter area 470 is for selecting an input parameter and its attributes for insertion in the formula. The input parameter area 470 contains a classification list 471 that the user can use to select the classification containing an input parameter. The input parameter area 470 further includes a parameter list 472 that shows all the parameters for the selected classification, which the user can use to select an input parameter from among the parameters contained in the selected classification. The input parameter area 470 also includes input parameter attribute selection controls 473 and 474. Input parameter attribute selection control 473 allows the user to select whether the calculation of the formula can proceed in the absence of any values for the selected input parameter. Input parameter attribute selection control 474 allows the user to select the time interval relative to the output parameter event time in which to identify events of the selected input parameter. The output parameter attribute selection control 474 allows the user to select intervals from day start time until output parameter event time, shift start time until output parameter event time, admit time until output parameter event time, or any other interval. The displayed interval actions preferably also include intervals from output parameter event time until day end time, output parameter event time to shift end time, and output parameter event time until discharge time (not shown). The input parameter area 470 further includes an input parameter insertion button 475, which the user may press to insert a reference to the selected parameter, having the selected input parameter attributes, at the insertion point in the formula window 422.

The command area 480 contains command buttons, including a dismiss command button 482, which the user may press to terminate the use of the visual interface; an apply command button, which the user may press to store the formula in the formula window 422 for the output parameter selected using the output parameter selection controls 411–412; and a delete command button 484, which the user may press to delete the contents of the formula window 422.

FIGS. 5–11 are screen diagrams illustrating the operation of the facility.

Figure 5:
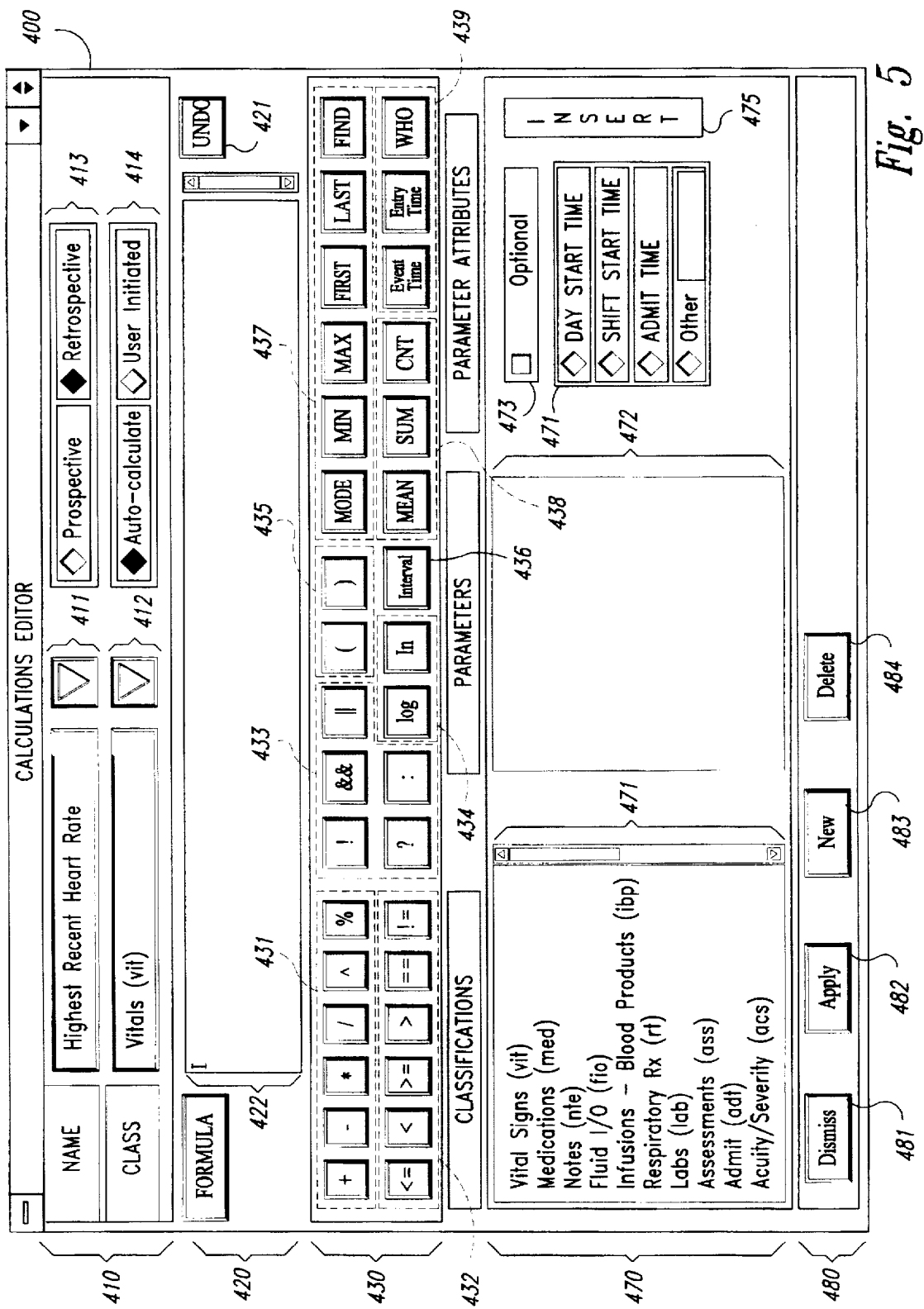
FIG. 5 is a screen diagram showing the selection of an output parameter.

FIG. 5 is a screen diagram showing the selection of an output parameter. The user has used output parameter selection control 412 to select a "Vital Signs (vit)" classification. The user then used output parameter selection control 411 to display the parameters contained in the Vital Signs group, and to select a "Highest Recent Heart Rate" parameter from the Vital Signs group as the output parameter. The user has also used an output parameter attribute selection control 413 to select "Retrospective," which specifies that input parameter intervals specified in the formula begin directly from the output parameter event time. The user could also have selected "Prospective," which would specify that input parameter intervals specified in the formula begin directly from an offset from the output parameter event time. This offset is preferably one hour after the output parameter event time. The user has also used an output parameter attribute selection control 414 to select "Auto-calculate," which specifies that the formula will be used to calculate values of the output parameter only in response to a specific user instruction.

Figure 6:
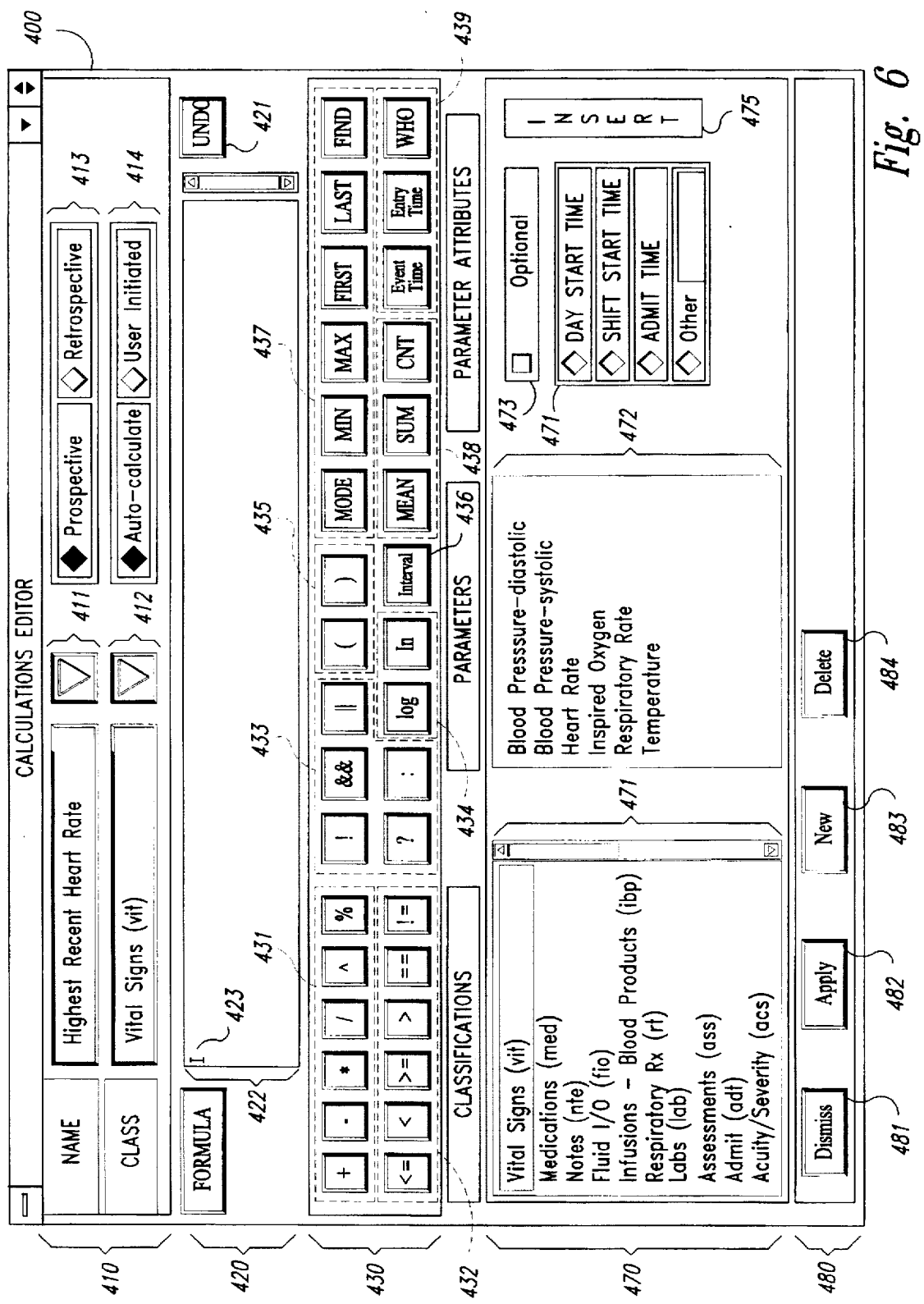
FIG. 6 is a screen diagram showing the selection of an input parameter classification.

FIG. 6 is a screen diagram showing the selection of an input parameter classification. The user has used the classification list 471, which displays the names of the classifications, to select the Vital Signs classification. In response, the facility has displayed the names of the parameters contained by the Vital Signs classification in the parameter list 472.

Figure 7:
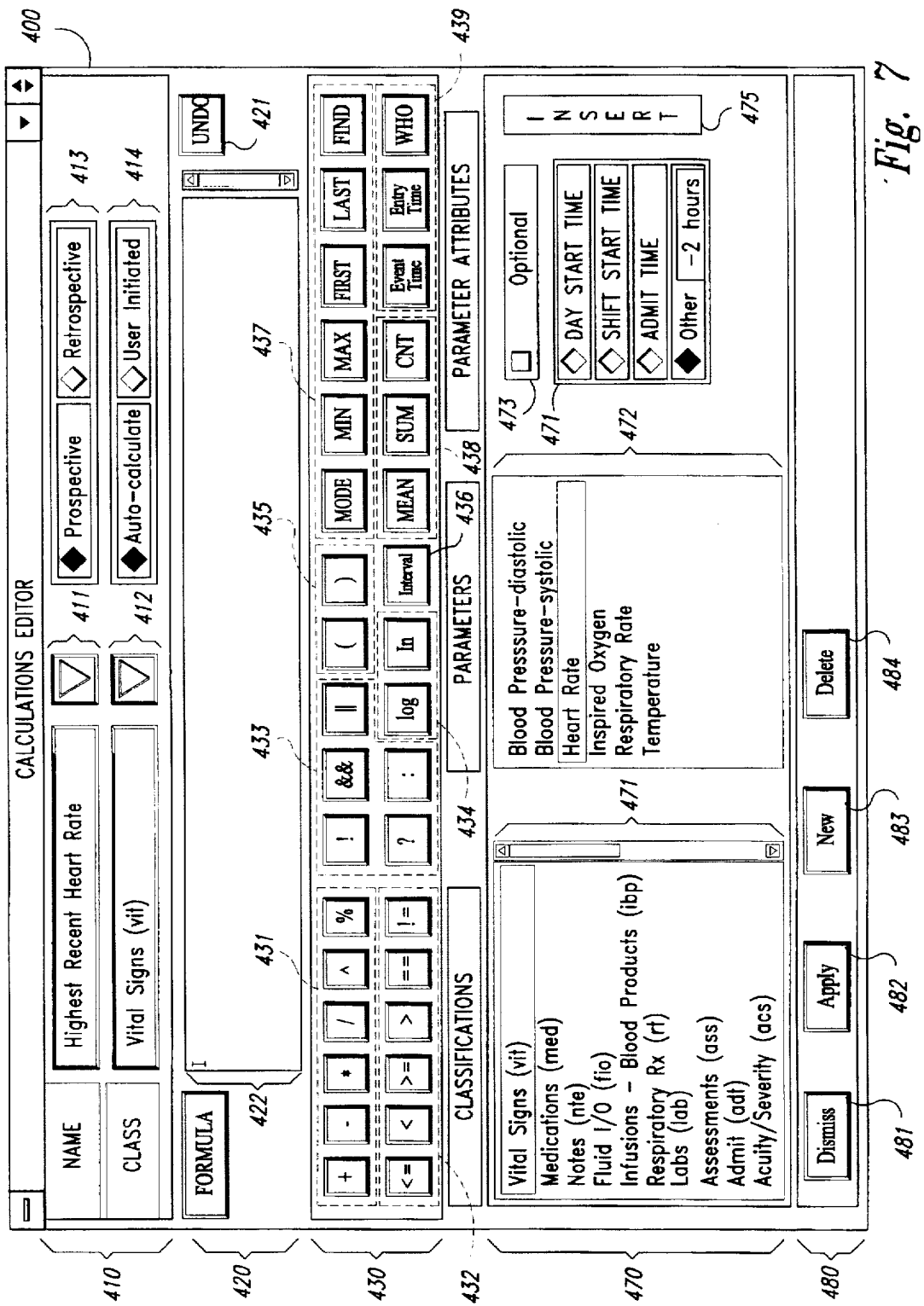
FIG. 7 is a screen diagram showing the selection of an input parameter.

FIG. 7 is a screen diagram showing the selection of an input parameter. The user has selected the Heart Rate parameter in the parameter list 472. The user has also used input parameter attribute selection control 473 to specify that the Heart Rate parameter is not optional, and that at least one event must be stored for this parameter before calculation of the present formula can proceed. The user has further used input parameter attribute selection control 474 to specify that the interval for which events of the Heart Rate parameter should be identified extends two hours backward in time from the starting point. The user could instead have specified that the interval extends forward in time from the starting point by inputting a negative interval. The user could also have specified that the interval extends backward or forward in time to one of the fixed times displayed in input parameter attribute selection control 474.

Figure 8:
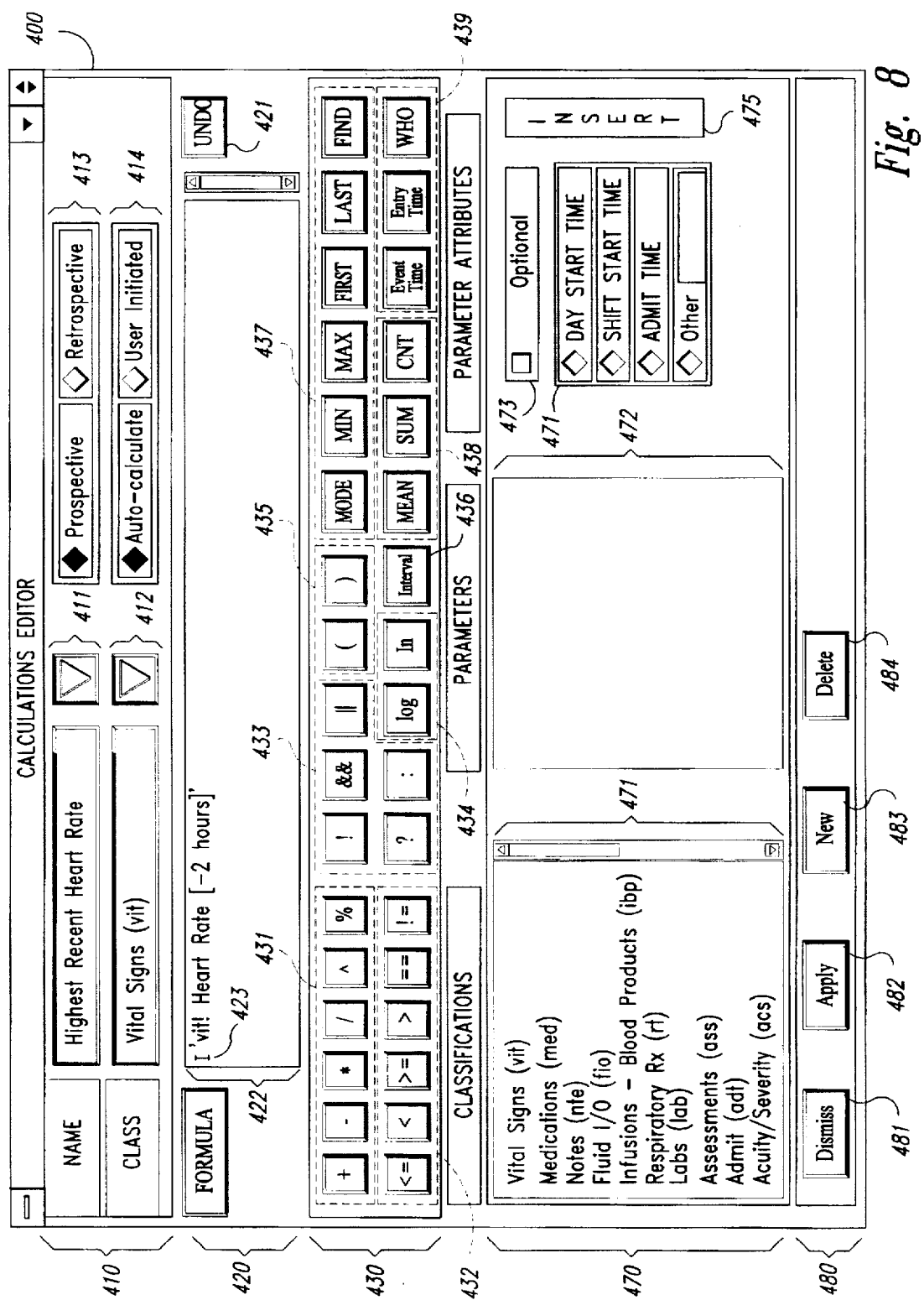
FIG. 8 is a screen diagram showing the insertion of a reference to an input parameter.

FIG. 8 is a screen diagram showing the insertion of a reference to an input parameter. The user has pressed the input parameter insertion button 475, causing the facility to insert a reference to the Heart Rate parameter, having the selected input parameter attributes, at the insertion point in the formula window 422. The formula window 422 therefore now contains the inserted reference to the Heart Rate parameter specifying the selected attributes discussed above:

'vit! Heart Rate [−2 hours]'

The user has also used the pointing device or keyboard to move the insertion point 423 from the end of the parameter reference to the beginning of the parameter reference in preparation for further input.

Figure 9:
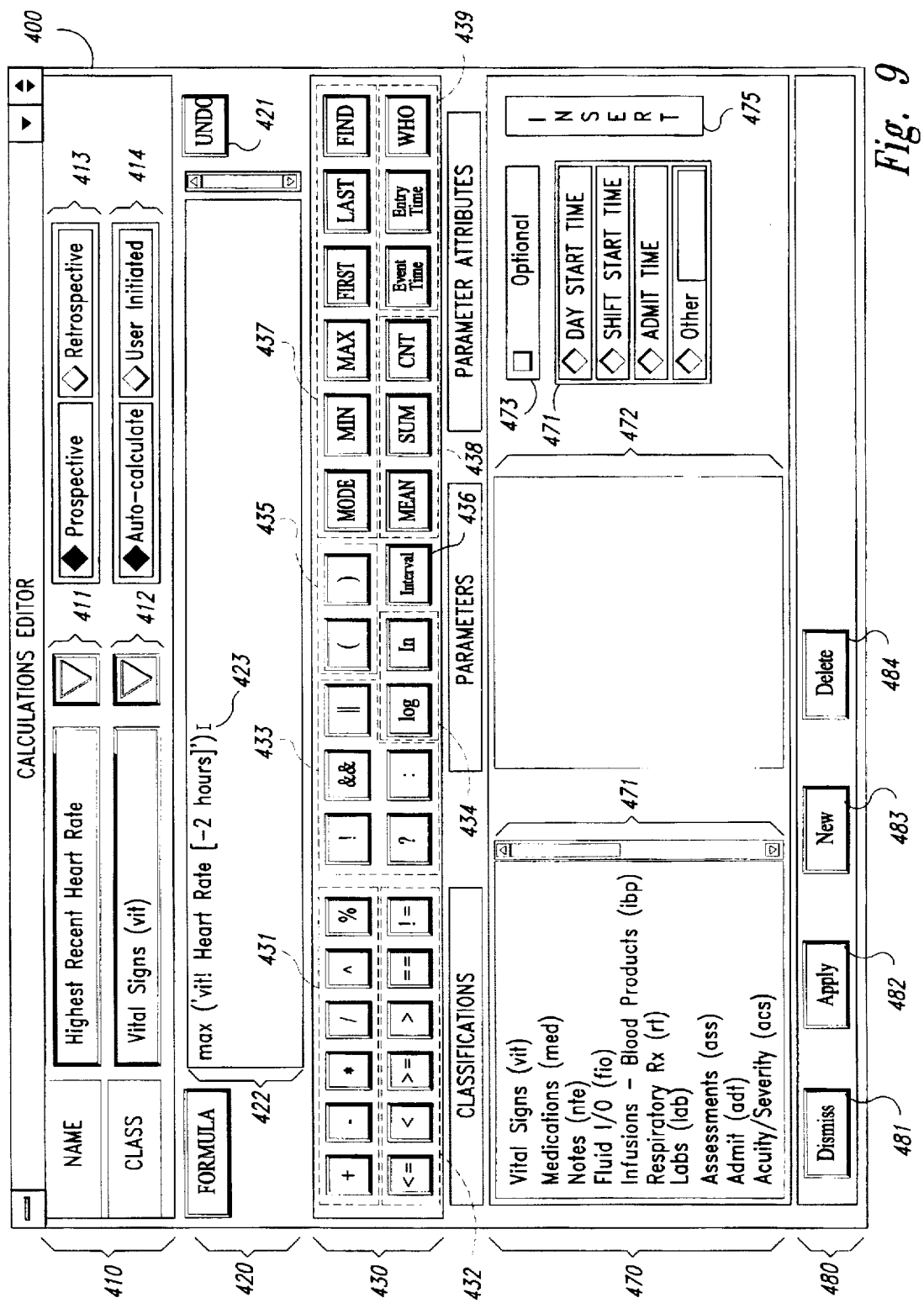
FIG. 9 is a screen diagram showing the insertion of an event selection function.

FIG. 9 is a screen diagram showing the insertion of an event selection function. The user has pressed the MAX button among the event selection function buttons 437, inserting "max," the name of the Maximum event selection function, in front of the parameter reference in the formula window 422. Each of the event selection functions receives an identified list of parameter events, represented by a parameter reference, as an argument and returns one of the events in the list. The Maximum event selection function selects the event in the list having the largest value. The user also could have chosen the Minimum event selection function, which selects the event having the smallest value; the Mode event selection function, which selects one of the events having the most common value; the First event selection function, which selects the event having the earliest event time; the Last event selection function, which selects the event having the latest event time; or the Find event selection function, which selects the event having the earliest event time which satisfies a condition specified by a second argument. As an example of the Find event selection function, the user could use the facility to generate the formula:

find (Heart Rate [−24 hours]>=120)

to select the first Heart Rate parameter event in the preceding 24 hours whose value was at least 120 beats per minute.

Instead of an event selection function button 437, the user could have pressed an aggregation function buttons 438 to insert an aggregation function. Aggregation functions, like event selection functions, receive an identified list of parameter events, represented by a parameter reference, as an argument. Unlike event selection functions, aggregation functions return a single value rather than an event. Aggregation functions include common statistical functions, such as Mean, Sum, and Count. In addition to inserting the name of the Maximum function, the user further used grouping buttons 435 to insert parentheses on either side of the parameter reference, making the parameter reference the argument of the Maximum event selection function.

Figure 10:
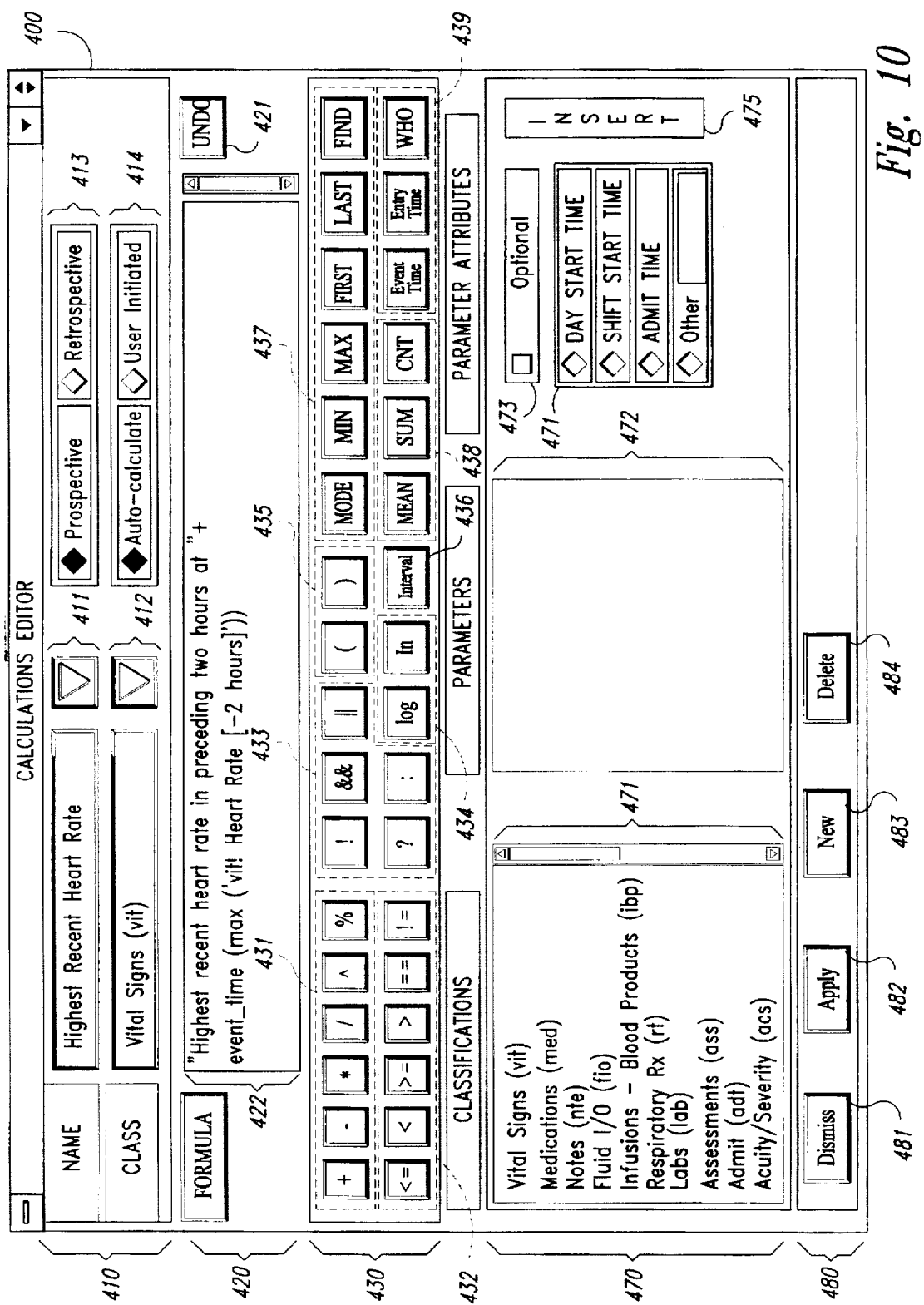
FIG. 10 is a screen diagram showing the use of event modifiers and textual values.

FIG. 10 is a screen diagram showing the use of event modifiers and textual values. The user has pressed the EVENT TIME button the event modifier buttons 439, inserting "$event_{13}$ time," the name of the Event Time event modifier, in front of the name of the Maximum event selection function in the formula window 422. Each of the event modifiers receive a single event as an argument and return a different component of the event. The Event Time event modifier returns the effective time of the event, while the Entry Time event modifier returns the time at which the event was entered and the Who event modifier returns the name of the person who entered the event. An event that appears without an event modifier represents the event value of the event. The user also used grouping buttons 435 to insert parentheses on either side of the Maximum event selection function, making the Maximum event selection function the argument of the Entry Time event modifier. The user further used the keyboard 107 to type an introductory string, and used the concatenation operator button to insert the concatenation operator between the introductory string and the effective time of the Heart Rate event having the highest value. After the user presses the apply button 482, events of the Highest Recent Heart Rate parameter will be generated using the formula in the formula window 422. The value of any such event of the Highest Recent Heart Rate parameter will be:

"Highest recent heart rate in preceding two hours at <$event_{13}$ time>" In the above, "<$event_{13}$ time>" is the effective time of the Heart Rate parameter event having the highest value at an effective time within two hours before the event time of the Highest Recent Heart Rate parameter event.

Figure 11:
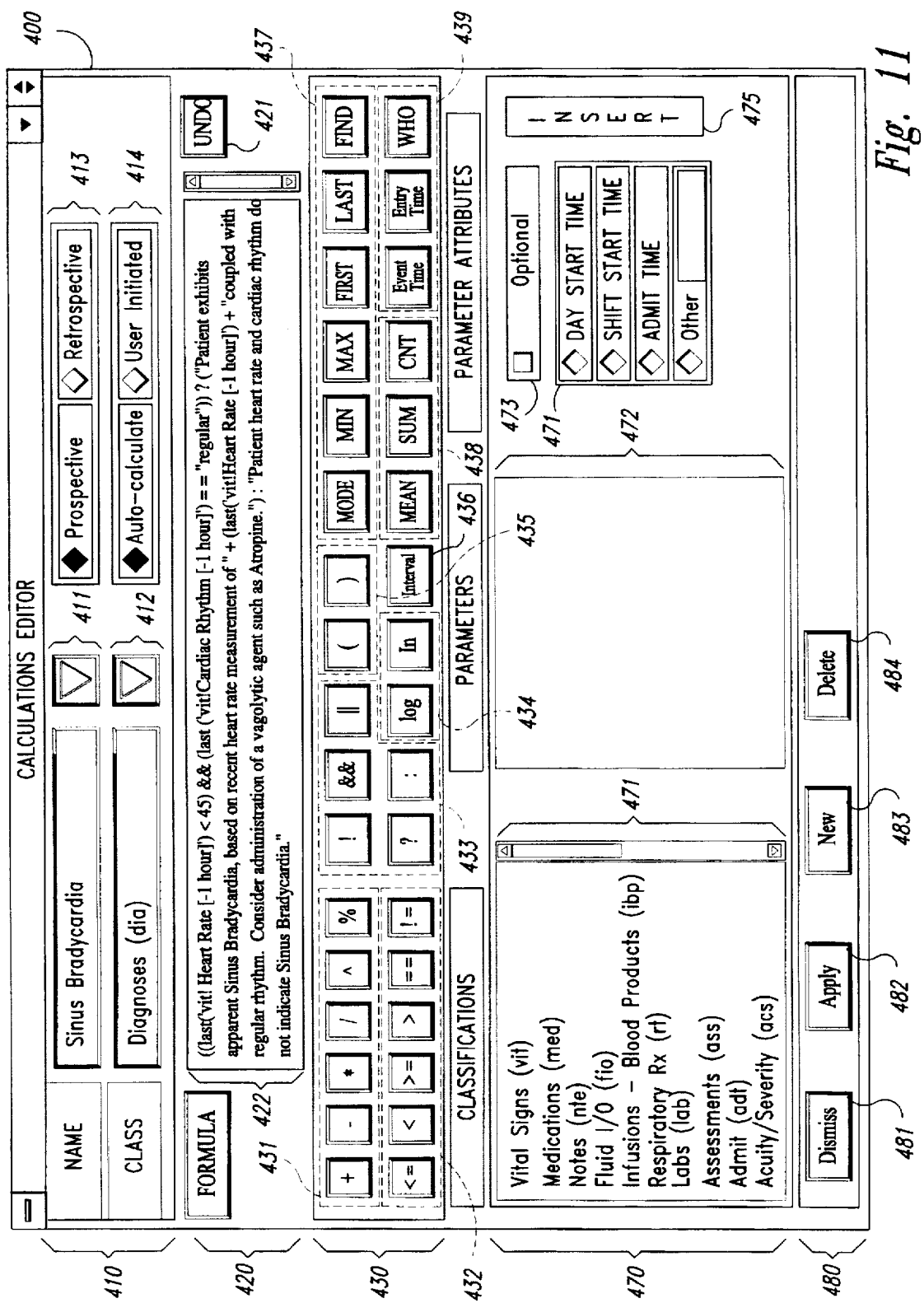
FIG. 11 is a screen diagram showing a formula constructed using the facility that generates a preliminary medical judgment and a corresponding treatment recommendation.

FIG. 11 is a screen diagram showing a formula constructed using the facility that generates a preliminary medical judgment and a corresponding treatment recommendation. It should be noted that this formula has been simplified for presentation as an example, and therefore omits substance necessary to generate a preliminary medical judgment and a corresponding treatment recommendation that justifies a reasonable level of confidence. Those of ordinary skill in the art may nonetheless use the formula shown in FIG. 11 as a model to construct formulae that generate preliminary medical judgments and treatment recommendations having confidence levels sufficiently high to benefit patient care.

FIG. 11 shows a formula constructed for a "Sinus Bradycardia" parameter of the Vital Signs classification. The term Sinus Bradycardia describes a dangerous drop in heart rate, which indicates the administration of a vagolytic agent to elevate heart rate to a safe level. The formula displayed in the formula window 422, reproduced below, attempts to preliminarily diagnose Sinus Bradycardia in patients for which Heart Rate and Cardiac Rhythm events are being recorded, based on the values of the most recent events recorded for these parameters. The formula further suggests that the administration of a vagolytic agent in such cases be considered:

((last('vit! Heart Rate [−1 hour]')<45) && (last('vit! Cardiac Rhythm [−1 hour]')=="regular"))? ("Patient exhibits apparent Sinus Bradycardia, based on recent heart rate measurement of" +(last('vit! Heart Rate [−1 hour]')+"coupled with regular rhythm. Consider administration of a vagolytic agent such as Atropine.") : "Patient heart rate and cardiac Rhythm do not indicate Sinus Bradycardia."

The formula is designed using a conditional value-branching construct as follows, inserted in the formula by the user using logical operator buttons 433:

<condition>?<value1>: <value2>

If the condition is true, the construct evaluates to value1. On the other hand, if the condition is not true, the construct evaluates to value2. In the case of the formula, the condition is constituted of indicators of Sinus Bradycardia, value1 is a text string diagnosing Sinus Bradycardia and recommending treatment, and value2 is a text string indicating that Sinus Bradycardia is not indicated. The value of the formula is therefore the text string diagnosing Sinus Bradycardia in cases in which the indicators of Sinus Bradycardia are present. To construct the condition, the user used comparison operator buttons 432 to insert the less than and equal to comparison operators, and used an additional logical operator button 433 to insert the and logical operator.

Figure 12:
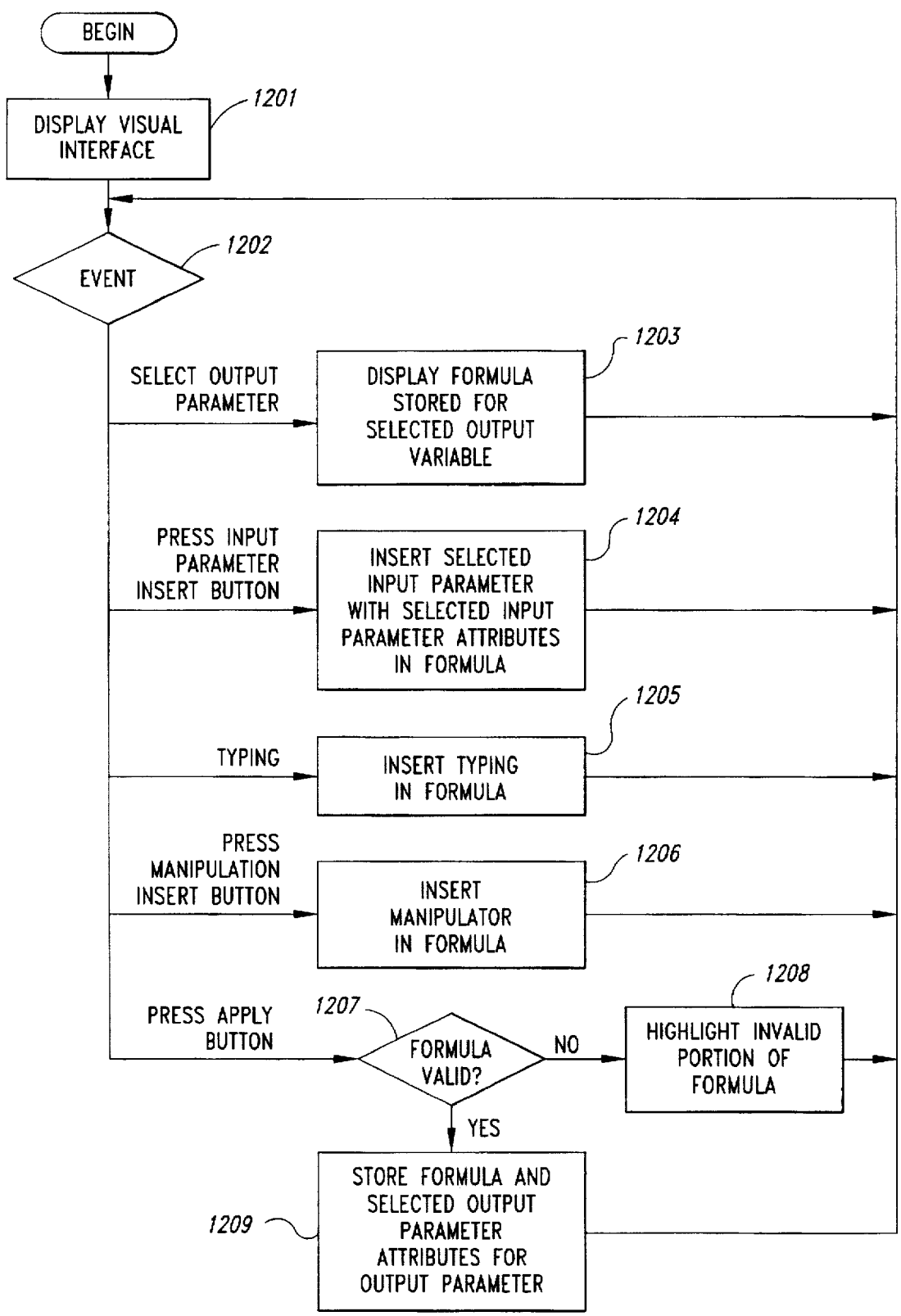
FIG. 12 is a flow diagram showing the steps that preferably comprise the facility.

The facility is preferably implemented as an event-handling program that receives and responds to interaction events generated by the user. FIG. 12 is a flow diagram showing the steps that preferably comprise the facility. In step 1201, the facility displays the visual interface as shown in FIG. 4. In step 1202, the facility waits for a user interaction event.

The next step performed by the facility is determined by the nature of the user interaction event received in step 1202. If the user interaction event received in step 1202 indicates that the user selected an output parameter using the output parameter selection controls 410, then the facility continues at step 1203 to display the formula stored for the selected output parameter in the formula window 422. If the user interaction event received in step 1202 indicates that the user pressed the input parameter insertion button 475, then the facility continues at step 1204 to insert the input parameter selected in parameter list 472 and the input parameter attributes selected in input attribute parameter controls 473–474 in the formula window 422 at the current insertion point. If the user interaction event received in step 1202 indicates that the user typed using the keyboard 107, then the facility continues at step 1205 to insert the text typed in the formula window 422 at the current insertion point. If the user interaction event received in step 1202 indicates that the user pressed one of the manipulator insertion buttons 430–439, then the facility continues at step 1206 to insert the manipulator of the pressed button in the formula window 422 at the current insertion point. Finally, if the user interaction event received in step 1202 indicates that the user pressed the apply button 482, then the facility continues at step 1207. In step 1207, if the formula appearing in the formula window 422 is valid, then the facility continues at step 1209, else the facility continues at step 1208. In step 1208, the facility highlights the invalid portion of the formula in the formula window 422. In step 1209, the facility stores the formula appearing in the formula window 422 and the output parameter attributes selected in the output parameter attribute selection controls 413–414 for the output parameter selected in the output parameter selection controls 410. The facility also preferably handles standard events for managing the state of visual controls such as the list boxes and check boxes displayed as part of the visual interface in step 1201 (not shown).

After any of steps 1203, 1204, 1205, 1206, 1208, or 1209, the facility continues at step 1202 to receive the next user interaction event.

The user may use the facility to construct a formula whose output parameter is an input parameter for one or more other formulae. The output parameter generated by such a formula is called an "intermediate parameter." Intermediate parameters may have independent clinical significance, and for that reason may be displayed by the automated medical patient information system. For example a first formula may generate a Glasgow scale intermediate parameter for gauging a patient's level of neurological responsiveness. Clinicians will recognize that the Glasgow scale intermediate parameter is useful both immediately to assess the patient's condition, and is also useful as an input parameter for a formula that determines the patient's Apache II severity score, which is a more comprehensive characterization of patient condition. On the other hand, an intermediate parameter may be of insubstantial clinical significance, and therefore may be unlikely to be displayed. For example, an intermediate parameter that is the sum of the volumes of all intravenous infusions may be used as an input parameter to a formula for calculating a patient's total fluid intake, but may otherwise be of little interest.

While this invention has been shown and described with reference to preferred embodiments, it will be understood by those skilled in the art that various changes or modifications in form and detail may be made without departing from the scope of the invention.

I claim:

1. A method in a computer system for constructing, in response to input from a user using a window-based user interface, a formula for producing a textual patient information string from a selected time-indexed medical data variable having a value for each of a plurality of times, the method comprising the steps of:

receiving input via the window-based user interface specifying a period of time during which the medical data variable is to be analyzed;

displaying via the window-based user interface names of a plurality of functions capable of aggregating a plurality of values into a single value;

receiving input via the window-based user interface indicating that the user selected the name of a selected function from the displayed function names;

receiving input via the window-based user interface specifying a manner of manipulating a single value to produce a textual string conveying patient information; and based upon the receiving steps, creating a formula that specifies:

identifying values of the selected time-indexed medical data variable having times within the specified period of time, applying the selected function to the identified values of the selected time-indexed medical data variable to aggregate the identified values into a single value, and manipulating the single value in the specified manner to produce a textual string conveying patient information based on the values of the selected time-indexed medical data variable, such that the formula may be used to generate and display a textual string conveying patient information based on the values of the selected time-indexed medical data variable.

2. The method of claim 1 wherein the selected time-indexed medical data variable is one of a plurality of time-indexed medical data variables each having a name, further including the steps of:

displaying via the window-based user interface the names of the plurality of time-indexed medical data variables; and receiving via the window-based user interface input indicating that the user selected the name of the selected time-indexed medical data variable from the displayed variable names.

3. A method in a computer system for constructing, in response to input from a user using a window-based user interface, a formula based on one or more of a plurality of time-indexed medical values, each time-indexed medical value having a name and being capable of having associated with it one or more individual medical values each having an effective time at which the individual medical value reflected the condition of a patient, the constructed formula having an effective time and referencing subsets of the individual medical values of each parameter upon which it is based whose effective times occur within a specified interval, the constructed formula being usable to generate individual medical values of a new time-indexed medical value, the method comprising the steps of:

displaying via the window-based user interface a list of the names of the time-indexed medical values;

receiving input via the window-based user interface identifying a time-indexed medical value whose name the user has selected from the displayed list of time-indexed medical value names;

displaying via the window-based user interface a list of time intervals for qualifying individual values of the identified time-indexed medical value;

receiving input via the window-based user interface identifying a time interval that the user has selected from the displayed list of time intervals;

displaying via the window-based user interface a list of functions for reducing the individual values of the identified time-indexed medical value whose effective times are within the identified time interval to a single value;

receiving input via the window-based user interface identifying a function that the user has selected from the displayed list of functions; and storing a formula for applying the identified function to individual values of the identified time-indexed medical value whose effective times are within the identified time interval in order to reduce the individual values to a single value, such that the stored formula may be used to generate individual medical values for a new time-indexed medical value.

4. The method of claim 3 wherein the single value to which the identified function of the formula stored in the storing step reduces the individual values is a numerical value.

5. The method of claim 3, further including the steps of:

determining whether the stored formula is invalid; and if the stored formula is invalid, displaying the formula via the window-based user interface such that the portion of the formula that is invalid is highlighted.

6. A method in a computer system for constructing, in response to user interface interactions by a user using a window-based user interface, a formula for deriving a medical conclusion from one of a plurality of time-indexed medical data inputs, the time-indexed medical data inputs each having events, the events each having multiple data components including a time, the method comprising the steps of:

receiving input via the window-based user interface identifying a time-indexed medical data input upon which the formula is to be based;

receiving via the window-based user interface an instruction identifying a time interval qualifying the events of the identified time-indexed medical data input;

receiving via the window-based user interface an instruction identifying a selection function for selecting one event from the events of the time-indexed medical data input qualified by the identified time interval;

receiving via the window-based user interface an instruction identifying a data component of each event of the time-indexed medical data input; and storing a formula for applying the identified selection function to events of the identified time-indexed medical data input whose effective times are within the identified time interval in order to select one of the events, and for extracting the identified data component of the selected event, such that the formula may be used to derive and display a medical conclusion from the identified time-indexed medical data input.

7. An apparatus for constructing, in response to input from a user using a window-based user interface, a formula for producing a textual patient information string from a selected time-indexed medical data variable having a value for each of a plurality of times, the method comprising the steps of:

a formula construction subsystem for constructing a formula for producing a displayable textual patient information string from a selected time-indexed medical data variable;

a display device coupled to the formula construction subsystem to display via the window-based user interface names of a plurality of functions capable of aggregating a plurality of values into a single value;

an input device coupled to convey to the formula construction subsystem from the user:

input specifying a period of time during which the medical data variable is to be analyzed, input indicating that the user selected the name of a selected function from the displayed function names, and input specifying a manner of manipulating a single value to produce a textual string conveying patient information; and a memory coupled to the formula construction subsystem to store a formula that specifies:

identifying values of the selected time-indexed medical data variable having times within the specified period of time, applying the selected function to the identified values of the selected time-indexed medical data variable to aggregate the identified values into a single value, and manipulating the single value in the specified manner to produce a textual string conveying patient information based on the values of the selected time-indexed medical data variable.

8. The apparatus of claim 7 wherein the selected time-indexed medical data variable is one of a plurality of time-indexed medical data variables each having a name, and wherein the display device is also coupled to display the names of the plurality of time-indexed medical data variables, and wherein the input device is also coupled to convey input indicating that the user selected the name of the selected time-indexed medical data variable from the displayed variable names.

9. The apparatus of claim 7 wherein the input device is a pointing device.

10. An apparatus for constructing a formula based on one or more of a plurality of time-indexed medical values in response to input from a user using a window-based user interface, each time-indexed medical value having a name and being capable of having associated with it one or more individual medical values each having an effective time at which the individual medical value reflected the condition of a patient, the constructed formula having an effective time and referencing subsets of the individual medical values of each parameter upon which it is based whose effective times occur within a specified interval, comprising:

a formula construction subsystem for constructing a formula based on one or more of the plurality of time-indexed medical values in response to input from a user;

a display device coupled to the formula construction subsystem to display via the window-based user interface:

a list of the names of the time-indexed medical values;

a list of time intervals for qualifying individual values of the identified time-indexed medical value, and a list of functions for reducing the individual values of the identified time-indexed medical value whose effective times are within the identified time interval to a single value;

an input device coupled to convey to the formula construction subsystem from the user:

input identifying a time-indexed medical value whose name the user has selected from the displayed list of time-indexed medical value names, input identifying a time interval that the user has selected from the displayed list of time intervals, and input identifying a function that the user has selected from the displayed list of functions; and a memory coupled to the formula construction subsystem to store a formula constructed by the formula construction subsystem for applying the identified function to individual values of the identified time-indexed medical value whose effective times are within the identified time interval in order to reduce the individual values to a single value, such that the formula stored in the memory may be used to generate individual values of a new time-indexed medical value.

11. The apparatus of claim 10 wherein the input device is a pointing device.

12. The method of claim 3, further comprising the step of generating individual values for the new time-indexed medical values using the stored formula.

13. The method of claim 12, further comprising the step of displaying the generated individual values for the new time-indexed medical values.

14. The method of claim 10, further comprising the step of generating individual values for the new time-indexed medical values using the stored formula.

* * * * *